US011236135B2

(12) United States Patent
Erhardt et al.

(10) Patent No.: US 11,236,135 B2
(45) Date of Patent: Feb. 1, 2022

(54) *SALMONELLA* AND IMMUNOGENIC COMPOSITION CONTAINING THE SAME AS WELL AS ITS USE

(71) Applicant: HELMHOLTZ-ZENTRUM FUR INFEKTIONSFORSCHUNG GMBH, Braunschweig (DE)

(72) Inventors: Marc Erhardt, Wolfenbuttel (DE); Sebastian Felgner, Braunschweig (DE); Dino Kocijancic, Braunschweig (DE); Siegfried Weiss, Braunschweig (DE)

(73) Assignee: HELMHOLTZ-ZENTRUM FUR INFEKTIONSFORSCHUNG GMBH, Braunschweig (DE)

( * ) Notice: Subject to any disclaimer, the term of this patent is extended or adjusted under 35 U.S.C. 154(b) by 0 days.

(21) Appl. No.: 16/607,756

(22) PCT Filed: Apr. 26, 2018

(86) PCT No.: PCT/EP2018/060747
§ 371 (c)(1),
(2) Date: Oct. 24, 2019

(87) PCT Pub. No.: WO2018/197621
PCT Pub. Date: Nov. 1, 2018

(65) Prior Publication Data
US 2020/0055904 A1 Feb. 20, 2020

(30) Foreign Application Priority Data
Apr. 27, 2017 (EP) ..................................... 17168323

(51) Int. Cl.
| C07K 14/255 | (2006.01) |
| A61K 35/74 | (2015.01) |
| C12N 1/36 | (2006.01) |
| C12N 15/52 | (2006.01) |

(52) U.S. Cl.
CPC ............ *C07K 14/255* (2013.01); *A61K 35/74* (2013.01); *C12N 1/36* (2013.01); *C12N 15/52* (2013.01)

(58) Field of Classification Search
None
See application file for complete search history.

(56) References Cited

U.S. PATENT DOCUMENTS

2011/0224097 A1\* 9/2011 Bramhill ............ C12N 15/1037
506/14

FOREIGN PATENT DOCUMENTS

| WO | 2013/084070 A2 | 6/2013 | |
| WO | WO-2013094070 A1 * | 6/2013 | ....... H01L 21/67132 |

OTHER PUBLICATIONS

Felgner et al. 2016 (aroA-Deficient *Salmonella enterica* Serovar Typhimurium Is More Than a Metabolically Attenuated Mutant; mBio 7(5):e01220-16. doi:10.1128/mBio.01220-16). (Year: 2016).\*
Deditius et al. 2015 (Characterization of Novel Factors Involved in Swimming and Swarming Motility in *Salmonella enterica* Serovar Typhimurium; PLoS ONE 10(8): e0135351; doi:10.1371/journal pone.0135351). (Year: 2015).\*
Felgner et al. 2016 (aroA-Deficient *Salmonella enterica* Serovar Typhimurium Is More Than a Metabolically Attenuated Mutant; mBio; vol. 7, Issue 5 e01220-16). (Year: 2016).\*
Felgner et al: "aroA-Deficient *Salmonella enterica* Serovar Typimuium Is More Than a Metabolically Attenuated Mutant", MBIO, vol. 7, No. 5, 2016-09.
Kocijancic et al: "Local Application of bacteria improves safety of <i>Salmonella</i> -mediated tumor therapy and retains advantages of systemic infection", ONCOTARGET, vol. 8, No. 30, Jul. 25, 2017.
Liu et al: "Outer membrane vesicles from flagellin-deficient *Salmonella enterica* serovar Typhimurium induce cross-reactive immunity and provide cross-protection against heterologous *Salmonella* challenge", Scientific Repoerts, vol. 6 No. 1, Dec. 1, 2016.
Stewart et al: "Regulation of phenotypic heterogeneity permits *Salmonella* evasion of the host caspase-1 inflammatory response", Proceedings of the National Academy of Sciences, vol. 108, No. 51, pp. 20742-20747, Dec. 5, 2011.
Leschner et al: "*Salmonella*-allies in the fight against cancer", Journal of Molecular Medicine, vol. 88, No. 8, pp. 763-773, Aug. 1, 2010.
Zheng et al: "Targeted Cancer Therapy Using Engineered *Salmonella typhimurium*", Chonnam Medical Journal, vol. 52, No. 3, p. 173, Jan. 1, 2016.
Ueno et al: "M Ring, S Ring and Proximal Rod of the Flagellar Basal Body of *Salmonella typhimurium* are Composed of Subunits of a Single Protein, FliF", Journal of Molecular Biology, vol. 227, pp. 672-677, 1992.
Berg: "Bacteria Swim by Rotating their Flagellar Filaments", Nature Publishing Group, vol. 245, Oct. 19, 1973.
Toso et al: "Phase 1 Study of the Intravenous Administration of Attenuated *Salmonella typhimurium* to Patients with Metastatic Melanoma", Journal of Clinical Oncology, vol. 20, No. 1, pp. 142-152, Jan. 1, 2002.

\* cited by examiner

*Primary Examiner* — Mary Maille Lyons
(74) *Attorney, Agent, or Firm* — W&C IP

(57) ABSTRACT

In a first aspect, the present invention relates to a mutated *Salmonella* strain comprising mutations in flagellin II genes, like the fliF gene, in particular, in addition the aroA gene, the IpxR gene, the pagP gene, the pagL gene, the ydiV gene and optionally the eptA gene and further optionally, the arnT gene. In a further aspect, immunogenic compositions comprising said *Salmonella* strain are provided optionally together with a pharmaceutically accepted carrier, diluent or effluent. Moreover, a method for producing outer membrane vesicles of *Salmonella* is provided, said method comprises the steps of cultivating the *Salmonella* strain according to the present invention and isolating the outer membrane vesicles accordingly. The present invention provides the bacteria or the outer membrane vesicles (OMVs) obtainable by the methods according to the present invention and its use as a transport moiety or as an immunogenic composition, like a vaccine or immunotherapy platform espedaily for therapeutic treatment of cancer of tissue or blood.

14 Claims, 9 Drawing Sheets

SALMONELLA AND IMMUNOGENIC COMPOSITION CONTAINING THE SAME AS WELL AS ITS USE

In a first aspect, the present invention relates to a mutated *Salmonella* strain comprising mutations in flagellin II genes, like the fliF gene, in particular, in addition the aroA gene, the lpxR gene, the pagP gene, the pagL gene, and, optionally, the ydiV gene as well as optionally the eptA gene and, further optionally, the arnT gene. In a further aspect, immunogenic compositions comprising said *Salmonella* strain are provided optionally together with a pharmaceutically accepted carrier, diluent or effluent. Moreover, a method for producing outer membrane vesicles of *Salmonella* is provided, said method comprises the steps of cultivating the *Salmonella* strain according to the present invention and isolating the outer membrane vesicles accordingly. The present invention provides the bacteria or the outer membrane vesicles (OMVs) obtainable by the methods according to the present invention and its use as a transport moiety or as an immunogenic composition, like a vaccine or immunotherapy platform especially for therapeutic treatment of cancer of tissue or blood.

PRIOR ART

Cancer ranks among the diseases that have experienced the least form of improvements in prevention and therapy over the last century based on incidence- and mortality rates. Therefore, it retains a position as the second most frequent cause of death, with no cure available to date. This thread is imminent due to an increasing incidence with age, and an expanding elderly population. Further, cancer represents a great socio-economic burden. Thus, there is an ongoing need for cost-efficient, effective and general type of cancer therapy.

An approach in cancer therapy is the use of infectious agents, e.g. bacteria mediated tumor therapy (BMTT) as a form of immunotherapy in the treatment of cancer. Promising strategies to target solid tumors based on BMTT have been described and the research community has fostered potent bacterial vector strains of the genera *Salmonella, Clostridia, Escherichia* and *Listeria* for more than a century. Many of the strains derived over this period of time have been successfully applied in preclinical and clinical trials.

Bacteria as therapeutic agents exhibit many advantages over conventional therapies such as surgery or chemotherapy: (i) their unique ability to specifically colonize tumors from a distant site of inoculation allows targeting of nearly all tumors present, including metastases, but also leukemia (ii) during the process of tumor colonization, the bacteria overcome physiological barriers which otherwise pose a limit to e.g. chemotherapy and (iii) because of an intrinsic tumor colonizing ability, engineered bacteria could be exploited as tumor targeting vectors for delivery of genetic cargo.

Despite these advantages, the immune system of the host could represent a major obstacle for BMTT. The intrinsic efficacy of BMTT relies on the capability of the bacteria to induce, reactivate or amplify a preexisting immune response against the tumor. It was shown that systemic or intratumoral inoculation of bacteria allows to induce first the innate immune system. Subsequently based on an adaptive immune response including cytotoxic T-cells, tumor clearance may occur.

However, the problematic inverse connection between safety and therapeutic potency remains a hurdle in strategies deployed in BMTT. The question also remains whether antibacterial immunity could interfere with therapeutic benefit of the bacteria in an immune competent host. In recent time, the predominant focus in BMTT has been placed on the Gram-negative bacterium *Salmonella*, like *Salmonella enterica* serovar *Typhimurium* (S. *Typhimurium*). The advantage of *Salmonella* includes an intrinsic therapeutic effect and a unique ability to specifically colonize tumors. The latter has also been exploited as strategy to deliver genetically encoded cargo directly into the tumor. Numerous examples and different designs highlight the versatile potential of such bacterial vectors as a highly promising cancer-therapeutic solution.

Today, *S. Typhimurium* is administered by intravenous or intratumoral infection. Numerous groups have consistently shown in a wide range of preclinical models that *Salmonella* is able to colonize cancerous tissue specifically with ratios of more than 1000:1 compared to healthy tissues such as liver and spleen, e.g. Leschner S. et al., PLoS One, 2009; 4:11. However, bacteria of above $10^6$ CFU per gram tissue in healthy organs may restrict dosing regimens and inflict severe side effects. On the other hand, avoiding such problems by excessive attenuation of *Salmonella* has been proven to cause loss of intrinsic potency in vivo for example demonstrated in clinical trials with *Salmonella* VNP20009, see Toso J F, et al., J. Clin Oncol. 2002, 20:142-52.

That is, *Salmonella* strains are in the focus of BMTT, however, the *Salmonella* strains available do not balance the requirements on safety and therapeutic potency sufficiently.

Most of the researches nowadays seek to ensure safety via genetic manipulation, local applications may still provide a suitable strategy to retain virulence while exhibiting a better safety profile. However, important criteria for successful local application should include: i) sustained advantages as found with systemic infection, ii) improved efficacy per comparable dose, and iii) a better safety profile.

Recently, the present inventors described an aroA-deficient *Salmonella enterica* serovar *Typhimurium* strain showing an enhanced immunogenicity, Feigner S., et al., mBio, 2016, 7: e01220-16. Further, the present inventors described a *Salmonella* bacteria conditionally modified in the LPS phenotype exhibiting a safe tumor targeting phenotype, see Frahm M., et al, mBio, 2015, 6:e00254-15.

A description of the flagella and the flagella basal body of *Salmonella* is given in Ring, M., et al, J. Mol. Biol., 1992, 227, 672-677. Further, Stewart M. K., et al., PNAS, 2011, 108 (51) 20742-20747 describe a regulation of phenotypic heterogeneity in *Salmonella* evasion of host caspase-1 inflammatory response describing the YdiV molecule as a regulatory mechanism producing bistability of the expression of flagellin.

The flagellum is a sophisticated macromolecular machine made of approximately 25 different proteins and can be divided into three main parts: 1) a basal body that is embedded in the cytoplasmic membrane and traverses the periplasm and cell wall up to the outer membrane (the engine), 2) a long external filament (the propeller) and 3) a flexible, curved structure known as the "hook" which connects the basal body with the rigid filament (Berg H C et al. Nature. 245(5425):380. (1973)).

The flagellar biosynthesis is tightly controlled at both transcriptional and post-translational levels. At a transcriptional level, flagellar gene expression is hierarchically organized. The flhDC master regulatory operon is under control of a class 1 promoter and activated in response to a plethora of environmental signals (Soutourina O A, Bertin P N. 2003. FEMS Microbiol Rev 27:505-523). The master regulatory complex, $FlhD_4C_2$, activates gene expression from class 2 promoters. Once the hook-basal-body (HBB) complex is completed, genes under control of class 3 promoters, including genes coding for the filament, motor-force generators and chemosensory system, are de-repressed.

Transcriptional regulation of the flagellar master regulator is complex and controlled by numerous global transcriptional regulators, which act on the level of the class 1 promoter of flhDC (e.g. RcsB, RflM, HilD, LrhA) (https://www.ncbi.nlm.nih.gov/pmc/articles/PMC4563271). Post-translational regulation of $FlhD_4C_2$ is dependent on the degenerate EAL domain-containing protein RflP (formerly YdiV, now Regulator of FlhDC Proteolysis, which targets $FlhD_4C_2$ protein complexes to proteolytic degradation by ClpXP protease (Stewart M. K., et al., PNAS, 2011, 108 (51) 20742-20747). In the present description it will still be called ydiV. The class 2 genes build up the transport gate to shuttle proteins from the intracellular to the extracellular space, and may play a crucial role during flagella synthesis. Thus interfering with particular genes of this operon (e.g. fliOPQR, flhlBA, fliHIJ, fliF or fliGMN) may promote OMV production.

Recently, the inventors have described an improved strain expressing a hexaacylated Lipid A (Feigner et al., Gut Microbes. 2016; 7(2): 171-177). The Lipid A is the hydrophobic anchor of the LPS molecule and is known to directly interact with the Toll-like receptor 4 (TLR-4-)-MD2 complex. *Salmonella* is able to modulate the structure of Lipid A by various genes such as pagP, pagL and IpxR in order to reduce or avoid immune recognition. It is known that acylation of Lipid A in *Salmonella* is heterogeneous. However, only a hexa-acylated Lipid A structure stimulates TLR-4 with high affinity while tetra-acylated Lipid A acts as an antagonist. For cancer therapy, a maximally stimulating bacterium is therapeutically beneficial. To avoid in vivo adaptation by expressing a tetra-acylated Lipid A, the 3 genes pagP, pagL and IpxR can be deleted. Homogenous expression of hexa-acylated Lipid A was achieved that way.

Recently, Liu Q., et al. (Scientific Reports, 6:34776, DOI: 10.1038/srep34776) disclose that outer membrane vesicles from flagellin-deficient *Salmonella enterica* serovar *Typhimurium* induce cross-reactive immunity and provide cross-protection against heterologous *Salmonella* challenge.

BRIEF DESCRIPTION OF THE PRESENT INVENTION

The present invention aims in providing new mutated *Salmonella* strains suitable in BMTT.

The present inventors were able to obtain mutated *Salmonella* strains having improved biosafety while being effective in therapeutic approaches.

In a first aspect, the present invention provides a mutated *Salmonella* strain comprising mutations in the flagellin class II genes. For example, the mutated *Salmonella* strain comprises mutations in the fliF gene, the ydiV gene, the aroA gene, the IpxR gene, the pagP gene and the pagL gene and optionally of the eptA gene.

That is, the present inventors recognized that surprisingly the mutations in the flagellin class II genes, like the synergy of the mutations in the fliF gene, the ydiV gene, the aroA gene, the IpxR gene, the pagP gene and the pagL gene results in a mutated *Salmonella* strain having superior properties both in biosafety as well as efficacy. In addition, it has been recognized that said mutated *Salmonella* strain having mutations in the flagellar class II genes, like the fliF gene, and optionally, the ydiV gene, the aroA gene, the IpxR gene, the pagP gene and the pagL gene further optionally, the eptA gene, an further optionally the arnT gene produce outer membrane vesicles (OMVs) in very high amounts suitable for various purposes. Moreover, the production of OMVs was surprisingly efficient in vivo, ex vivo and in vitro experimental conditions. These mutated *Salmonella* strains are characterized in being strains with hexa-acylated LipidA due to the mutations in the IpxR, the pagP and the pagL gene, without functional flagella but rich in immunostimulatory flagella proteins as well as auxotrophic for aromatic amino acids that are not freely available in large amounts in the mammalian host. Thus, this strain is limited to survive in vivo as the Shikimate biochemical pathway is abrogated by deleting the gene for aroA. It also down-regulates the arnT gene responsible for lipid A modification. Furthermore, it has been shown by the inventors that the gene deletion ydiV is not crucial for OMV synthesis in vitro. However, in vivo this deletion allows OMV and flagella protein production and the maximal therapeutic effect, because it is submitted that it influences the bacterial physiology to a large extend especially in vivo. Optional, the strain will contain a deletion of eptA responsible for further modification of lipid A to improve immunogenicity.

In a second aspect, the present invention relates to an immunogenic composition comprising the mutated *Salmonella* strain according to the present invention and, optionally, a pharmaceutically acceptable carrier, effluent or diluent.

The immunogenic composition is particularly useful as a vaccine or immunotherapeutic as well as in the use of preventing or treating tumors and cancer, in particular, solid tumors.

In a third aspect, the immunogenic composition is used in a method of treating a subject in need thereof by administering the immunogenic composition or the *Salmonella* strain according to the present invention by systemic parenteral, oral, intradermal, mucosal administration application, or locally by intratumor application or into the vicinity of the tumor or combinations thereof. Further, in case of a vaccine application, the immunogenic composition is administered by known application routes, like parenteral, systemic, oral, mucosal, intradermal, subcutaneous or intratumoral route.

A forth aspect relates to a method for producing outer membrane vesicles (OMVs) of *Salmonella* comprising the step of providing a *Salmonella* strain according to the present invention, culturing the same in a suitable culture medium and isolating outer membrane vesicles from the cultural supernatant and/or from the *Salmonella* strains.

In a fifth aspect, the present invention relates to the OMVs obtainable by a method according to the present invention.

Finally, the present invention relates in a further aspect to the use of said OMVs obtainable by the method according to the present invention or as described herein as well as to the use of the mutated *Salmonella* strains for representing a transport moiety for a predetermined compound. Said predetermined compounds are in particular antigens, toxic components, immunomodulatory molecules, small molecules, large molecules, proteins, peptides, DNA, RNA, antibodies or pro-drug converting enzymes. Said OMVs and mutated *Salmonella* strains are suitable for transporting the same to a target, in particular, a cell. Alternatively, the OMVs and mutated *Salmonella* strains are for use as an immunogenic composition, like a vaccine, or an immunotherapeutic composition. Finally, OMVs and mutated *Salmonella* strains can also be used as decoy targets to reduce the effect of pre-existing reactivity against pathogenic targets, autoimmunity or immunity against the specific bacterial vector.

OMVs can be produced in vitro, ex vivo or in vivo which is conferred by the unique combinations of mutations according to the present invention, e.g. inside the particular *Salmonella* strain SF200 described herein.

DETAILED DESCRIPTION OF THE PRESENT INVENTION

Definitions

Figure 1:
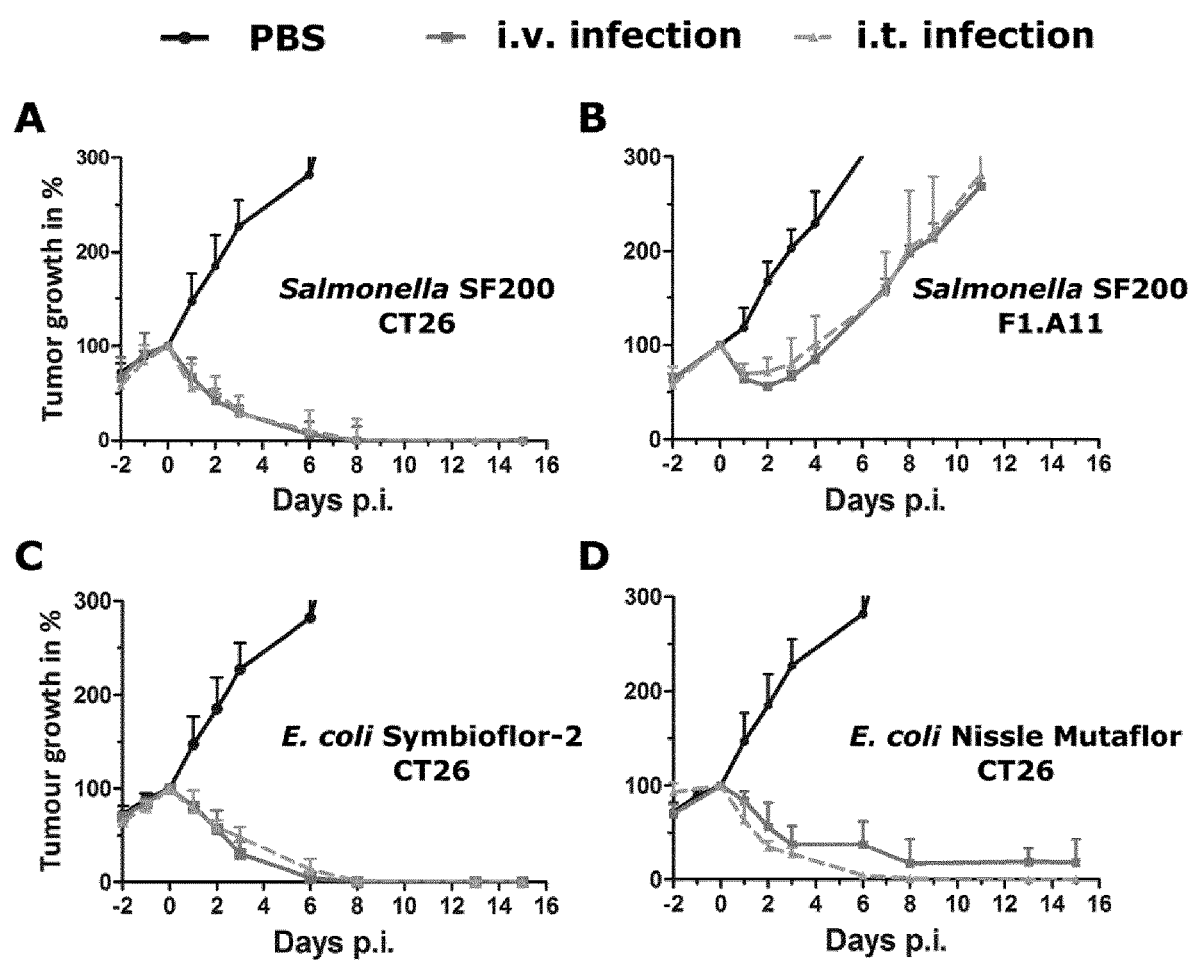
FIG. 1: Tumor development upon intravenous and intratumoral infection with *Salmonella* and probiotic *E. coli*. CT26 tumor-bearing mice were infected with $5 \times 10^6$ CFU SF200 ($\Delta$lpxR9 $\Delta$pagL7 $\Delta$pagP8 $\Delta$aroA $\Delta$ydiV MIT) (A), Symbioflor-2 (C) and *E. coli* Nissle (D). Considering more resilient tumors, F1.A11 tumor-bearing mice were infected with $5 \times 10^6$ SF200 (B). Straight lines depict i.v. infection and dotted lines i.t. infection. Tumor volumes were calculated on the basis of caliper measurements. PBS served as a negative control. Displayed are values of mean±SEM. Results are representative of two independent experiments with five replicates in each group.

Before the present invention is described in detail below, it is to be understood that this invention is not limited to the particular methodology, protocol and reagents described herein as these may vary. It is also to be understood that the terminology used herein is for the purpose of describing particular embodiments only and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions, gene bank accession number, sequence submissions etc.) whether supra or infra, is hereby incorporated by reference in its entirety. In the event of a conflict between definitions or teachings of such incorporated references and definitions or teachings cited in the present specification, the text of the present specification text precedence The term "comprise" or variants such as "comprises" or "comprising" as well as the term "contain" with its variations according to the present invention does not exclude the presence of other features or parameters not mentioned. The above terms include the term "consist" or variations thereof. The term "consist" or "consisting essentially of" is used herein interchangeably, according to the present invention means the specific features or parameters mentioned while excluding modifications or other parameters accordingly.

The term "a" and "an" and "the" and similar reference used in the contents describing the invention, especially in the context of the claims, are to be construed to cover both the single and the plural, unless otherwise indicated herein or clearly contradicted by the context.

The term "attenuated" refers to a strain rendered to be less virulent compared to the native strain, thus, becoming harmless or less virulent. Attenuated does not mean inactivated.

The term "mutated *Salmonella* strain" refers to *Salmonella* strains having mutations in the genes specified. That is, the mutated *Salmonella* strains are *Salmonella* strains having mutations in at least one of the flagellin class II genes. In an embodiment, said flagellin class II genes are at least one of the fliF gene and the fliHIJ genes. Other embodiments include at least one of the following genes: flip, fliO, fliQ, fliR, flhB, flhA, fliG, fliM or fliN.

According to an embodiment of the present invention, the *Salmonella* strain has mutations in the fliF gene, the ydiV gene, the aroA gene, the IpxR gene, the pagP gene and the pagL gene. Alternatively, the strain has mutations in other class II genes like the fliH, the fliI and the fliJ genes, in addition to the ydiV gene, the aroA gene, the IpxR gene, the pagP gene and the pagL gene. Optionally, the strain may contain a mutation in the eptA gene and, optionally, the arnT gene. The mutation may be any kind of mutation known to the skilled person including addition, deletion, and/or substitution of at least one nucleotide, thus, altering the coding or non-coding sequence of said gene resulting in alteration of the expression of the protein encoded by said gene or alteration of the amino acid sequence. In an embodiment, the mutation is a deletion of at least part of the specified gene including full deletion of said gene.

As used herein, the term "flagellin class II genes refers to the genes building up the transport gate to shuttle proteins from the intracellular to the extracellular space including the following genes:
fliF, fliP, fliO, fliQ, fliR, flhB, flhA, fliG, fliM, fliN, fliH, fliJ, fliI. Sometimes a combination of genes is mentioned, like fliGMN or fliHIJ as well as fliPOQR.

The fliF gene (STMUK_1948 according to KEGG terminology) refers to the gene encoding a membrane bound protein required for flagella synthesis (Ueno et al., 1992. Journal of Molecular Biology; 227(3):672-7)). Encoded by the ydiV (STMUK_1311) gene is a negative regulator of flagella synthesis (Takaya et al., 2012. Molecular Microbiology; 83(6):1268-84 and Wada et al., 2011. Journal of Bacteriology; 193(7):1600-1611). The aroA gene (STMUK_0944) confers safety by turning *Salmonella* auxotrophic for aromatic amino acids (Hoiseth et al., 1981. Nature; 291(5812):238-9). The genes encoding pagL (STMUK_2276), pagP (STMUK_0633) and IpxR (STMUK_1295) are involved in synthesis of Lipid A and ensure that Lipid A is homogenously hexa-acylated (Needham et al., PNAS; 110(4):1464-9). In addition, the further class II genes are as follows: flip, STMUK 1958; fliO, STMUK 1957; fliR, STMUK 1960; flhB, STMUK_1894; flhA, STMUK_1893; fliG, STMUK_1949; fliM STMUK_1955; fliN STMUK_1956; fliH STMUK_1950; fliJ STMUK_1952; fliI STMUK_1951.

In addition, the mutated *Salmonella* strains according to the present invention may contain additional mutations in the genes eptA as well as arnT both relate to the phosphorylation of lipid A. The arnT is shown in STMUK 2331 and eptA is STMUK 3304.

Lipid A is a glucosamine disaccharide that carries phosphate groups at positions 1 and 4'. Normally, these phosphate are modified by 4-amino-4-deoxy-L-arabinose (L-Ara4N) and phosphoethanolamine (pEtN), respectively. Such modifications result in decreased immunogenicity of the lipid A. Due to the aroA mutation the modifying (arnT) will be down-regulated, while the optional deletion of eptA will inhibit the modification of the second phosphate. It is submitted that the immunogenicity or adjuvanticity will be increased.

As demonstrated herein, the mutated *Salmonella* strain according to the present invention comprising mutations in the flagellin class II genes, like *Salmonella* strains comprising mutations in at least one of the following genes: fliF gene, fliHIJ gene, fliP, fliGMN, fliOPQR, and flhAB, fliH gene, fliI gene, fliJ gene, fliG gene, fliM gene, fliN gene, fliO gene, flip gene, fliQ gene, fliR gene, flhA gene, flhB gene demonstrates an improved biosafety while remaining efficient against cancer. In an embodiment, these *Salmonella* strains are at least mutated *Salmonella* strains comprising mutations in at least one of the fliF gene or the fliHIJ genes. In an embodiment, the mutated *Salmonella* strain according to the present invention comprises furthermore mutations in the ydiV gene. That is, a *Salmonella* strain having mutations in the fliF gene, the ydiV gene, the aroA gene, the lpxR9 gene, the pagL7 gene and the pagP8 gene as exemplified herein as well as the *Salmonella* strain having mutations in the lpxR9 gene, pagL7 gene, pagP8 gene, aroA gene, and fliHIJ genes exemplified herein demonstrate biosafety while having remarkable efficacy against cancer, in particular, solid tumors. Optional, the strains contain a deletion in the eptA gene and, optional, the arnT gene optimizing the immunogenicity of the *Salmonella* strains.

In an embodiment of the present invention, the *Salmonella* strain is a strain being modified insofar that mutations are present in the pagL7, pagL8 and lpxR9 gene. In an embodiment of the present invention, the mutations are combined with a mutations at least in one of the genes of the flagellin class II. For example, the *Salmonella* strain is a strain being modified at least in one of the genes of fliF or the fliHIJ genes. Further, a *Salmonella* strain is provided with the mutations in the pagL7, pagL8 and lpxR9 gene in combination with the mutations present in the ydiV (optionally) and fliF genes as well as the aroA gene. The aroA gene is known to be suitable as a metabolic mutation to attenuate *Salmonella*. aroA is part of the shikimate pathway which directly connects glycolysis to the synthesis of aromatic amino acids. aroA deficient *Salmonella* strains are described e.g. in Feigner S. et al, mBio 2016, see above. It also results in the down-regulation of arnT.

The *Salmonella* strain according to the present invention may be any *Salmonella* strain, however, suitable *Salmonella* strains include the *Salmonella enterica* species, in particular, the *Salmonella* strain being a *Salmonella enterica* SSP. *Enterica*, like a serovar *Typhimurium* or serovar *Thyphi* strain.

In a further aspect, the mutated *Salmonella* strain according to the present invention is an attenuated *Salmonella* strain. The skilled person is well aware of suitable methods for attenuating *Salmonella* strains including mutating particular genes, like the aroA gene as defined above or the gene purI (defective in purine synthesis) or the asd gene (defective in aspartate-semialdehyde dehydrogenase required for cell wall synthesis)

In an embodiment of the present invention, the mutated *Salmonella* strain according to the present invention is a *Salmonella* strain which is able to form an increased number of outer membrane vesicles whereby said outer membrane vesicles are characterized in containing no functional flagella but being increased in immunostimulatory flagella proteins and LPS as well as bacterial proteins, recombinant proteins small immune stimulatory or immune modulatory molecules, RNA and DNA.

The *Salmonella* strain according to the present invention demonstrates an improved safety profile while, at the same time, having increased immunostimulatory and cytotoxic capacity.

Furthermore, the *Salmonella* strain according to the present invention is able to overcome the efficacy-limiting effects of pre-exposure. While it is known for common vector strains including *Salmonella* and *E. coli* strains to be limited as a vaccine when the subject was pre-exposed thus limiting the efficacy of vaccination. The strain, according to the present invention demonstrates no efficacy limitation even after preexposure to *Salmonella*. That is, the strains according to the present invention have greater immunogenicity.

In addition, the outer membrane vesicles of the *Salmonella* strains according to the present invention are suitable for drug delivery as well as having improved immunomodulatory properties, thus, allowing its use in an immunogenic composition, like a vaccine or immunotherapeutic.

The *Salmonella* strain is a suitable vector for various therapeutic applications, in particular, for use in cancer therapy as well as other chronic or acute diseases. In particular, the vector is suitable as a vaccine, vaccine platform, immunotherapy or immunotherapy platform in prophylactic or therapeutic cancer therapy or additional chronic or acute diseases. As recognized by the present inventors, the strains according to the present invention are not limited in the efficacy due to pre-exposure to bacteria. This is in particular true for BMTT.

That is, in a further aspect the present invention relates to an immunogenic composition comprising the *Salmonella* strain as defined herein. Said immunogenic composition is particularly useful in cancer therapy as well as a vaccine platform or immunotherapy platform. On the one hand, said *Salmonella* strain may be used as it is, alternatively, the outer membrane vesicles derived from said *Salmonella* strain may be part of the immunogenic composition according to the present invention.

Said immunogenic composition optionally contains a pharmaceutically acceptable carrier, effluent or diluent. The skilled person in the art is well aware of suitable carriers, effluents or diluents accordingly. The skilled person will select suitable carriers, effluents or diluents based on the way of administration.

In an embodiment of the present invention, the immunogenic composition contains further an adjuvant. Suitable adjuvants are known to the skilled person including c-di-AMP, c-diGMP, cGAMP, CpG motifs, non-coding RNAs, mRNA, DNA, bacterial proteins, recombinant proteins, peptides, small molecules, large molecules and antibodies In a further aspect, the immunogenic composition according to the present invention or the mutated *Salmonella* strain according to the present invention is for use in the prophylaxis or treatment of solid tumors. It has been recognized that the *Salmonella* strain according to the present invention is superior in its biosafety properties as well as its immunostimulatory capacities compared to *Salmonella* strains known in the art. In particular, the mutations in the flagellin class II gene provides an improved biosafety to the *Salmonella* strain. In particular, combining the same with the mutations in the pagL7, pagL8 and lpxR9 gene demonstrates improved properties also having immunostimulatory capacities. In particular, the *Salmonella* strain SF200 is superior due to the synergy of the six mutations, the *Salmonella* strain according to the present invention is particularly useful in the treatment or prophylaxis of cancer and tumors, like solid tumors as well as for blood cancer and other chronic or acute diseases, the same holds true for the alternative *Salmonella* strains SF210 and SF211 exemplified herein.

The *Salmonella* strain according to the present invention is particularly useful in prophylaxis or treatment of subjects with pre-exposure to bacteria, in particular, *Salmonella* strains.

The term "solid tumors" refers generally to an abnormal mass of tissue that may be benign (not cancer), or malignant (cancer). Particular embodiments of the solid tumors include colon carcinoma, fibrosarcoma, renal cell carcinoma, melanoma, glioma, pancreas carcinoma, hepatoma, prostate carcinoma, bladder carcinoma and metastases thereof. Embodiments of other cancer include blood cancer including lymphoma and leukemia.

Further, the immunogenic composition or the *Salmonella* strain according to the present invention, in particular, for use in the prophylaxis or treatment of solid tumors may be used in any way of administration. Suitable ways include the systemic administration via known route and, in addition, the intra-tumoral application or the application into the vicinity of the tumor or combinations thereof.

Intra-tumoral application means that the bacterial formulation is injected in a low volume directly into the tumor mass. Application into the vicinity of the tumor refers to the injection of the bacterial formulation e.g. in a low volume into the tissue surrounding a tumor. Typically, vicinity refers to a distance of 1 cm at most from the palpable tumor tissue. like at most 0.8 cm, e.g. at most 0.5 cm.

In particular, the intra-tumoral application of the immunogenic composition according to present invention is suitable for treating solid tumors as identified herein. This is particularly shown for colon carcinoma, fibrosarcoma and renal cell carcinoma.

As demonstrated herein, the tumor models used herein allow to determine the sensitivity of the tumor model against *Salmonella*. While the colon cancer model was the most sensitive one, the renal cell carcinoma was in between the colon carcinoma and the fibrosarcoma. Thus, the three models mentioned herein, namely the colon carcinoma, fibrosarcoma and renal cell carcinoma model allow to determine efficacy of strains to be tested for BMTT.

Taking the biosafety into account, it is desired to administer the immunogenic composition by intra tumor application or in the vicinity of the tumor or combination of both. Surprisingly, this is also possible in case of treating cancer metastases.

In addition, it has been shown that CD8 T cell as well as a CD4 T cell memory is developed. This immunological memory may be particularly useful for avoiding recurrence.

It is submitted, that the immunological memory is already present before application of the bacteria. The immunogenic composition according to present invention allows to activate the same, thus, allowing treatment of the cancer and, in particular also of recurring cancer. Alternatively, the bacteria can be constructed to express antigens found in the cancer cells to be treated.

In a further aspect, the present invention relates to a method for producing outer membrane vesicles of *Salmonella*. The method according to the present invention comprises the steps providing a *Salmonella* strain as defined herein. The *Salmonella* strain is cultivated in a suitable culture medium whereby the skilled person is well aware of suitable culture media and culture conditions. After cultivation the outer membrane vesicles are isolated or enriched from the supernatant of the culture medium and/or from the *Salmonella*.

In an embodiment of the method for producing outer membrane vesicles the *Salmonella* strain provided produce active components, like toxins, immunomodulatory molecules or pro-drug converting enzymes whereby said toxic components, immunomodulatory molecules, DNA, RNA, proteins peptides small molecules, large molecules, antibodies or pro-drug converting enzymes are present in the outer membrane vesicles. Thus, it is possible to produce with the method according to the present invention outer membrane vesicles useful as a vaccine or immunotherapy platform or as a transport moiety in general for delivering compounds to a target. Of course, also the *Salmonella* strains according to the present invention may be used for the same purposes. Typically, said target is a cell. That is, it is possible to deliver otherwise toxic components target orientated to a predetermined target, e.g. cancer cells, allowing delivering toxic components or other components for killing said tumor cells or otherwise treating solid tumor cells or inferencing tumor cells. In addition, immunomodulatory molecules might be transferred to cancer of blood cells. Furthermore, immunomodulatory molecules might be transferred to immune cells involved in fighting or protecting cancer. Of course, said OMV may also contain other compounds like marker or label compounds useful for target orientated labeling of predetermined targets. In addition, the OMVs can be used to treat additional chronic diseases like chronic inflammatory diseases or acute diseases like infections. Further, OMVs may be useful as decoys in pharmaceutical compositions, e.g. in case of immune effectors administered to a subject, etc.

The outer membrane vesicles according to the present invention are also useful in immunogenic compositions as described herein. That is, it may not be necessary to include the *Salmonella* strain as such into the immunogenic composition but only the OMVs derived therefrom. That is, in another embodiment of the present invention the use of OMVs obtained by a method according to present invention or outer membrane vesicles according to present invention as i) a transport moiety for a compound, in particular, of toxic components, immunomodulatory molecules small molecules, large molecules, DNA, RNA, proteins, peptides or prodrug converting enzymes to a target, in particular a cell, or ii) an immunogenic composition, like a vaccine, iii) a decoy target to antibiotics, bacteriophages, antibodies or blood factors, like complement or cytokines, active components produced by pathogens, iv) to directly interact and manipulate host or cancer cells with an immunomodulatory, genotoxic or cytotoxic objective, v) as reaction platform to produce drugs in vivo, ex vivo or in vitro.

In a further aspect, the present invention relates to the use of a mutated *Salmonella* strain according to the present invention as i) a transport moiety for a compound, in particular, of toxic components, immunomodulatory molecules small molecules, large molecules, DNA, RNA, proteins, peptides or prodrug converting enzymes to a target, in particular a cell, or ii) an immunogenic composition, like a vaccine, iii) a decoy target to antibiotics, bacteriophages, antibodies or blood factors, like complement or cytokines, active components produced by pathogens, iv) to directly interact and manipulate host or cancer cells with an immunomodulatory, genotoxic or cytotoxic objective, v) as reaction platform to produce drugs in vivo, ex vivo or in vitro.

In a further aspect, the *Salmonella* strain according to the present invention or the OMVs according to the present invention may contain nucleic acid molecules, like DNA or RNA being under the control of a carbohydrate depending promoter. Such a carbohydrate depending promoter is exemplified by the Lac operon known to the skilled person. With this carbohydrate depending promoter it is possible to allow on/off of genes operably linked with said promoter. This is particularly helpful for transgenes coding for an antitumor agent or genes which are relevant for the infectivity of the *Salmonella* strain. The skilled person is well aware of suitable promoters allowing a carbohydrate depending on/off operation.

In another aspect of the present invention, a method is provided for preventing or treating cancer or for immunomodulation in a subject in need thereof. The mutated *Salmonella* strain according to the present invention or the outer membrane vesicles according to the present invention as well as the immunogenic composition according to the present invention are administered in a method according to the present invention to a subject in need thereof suffering from cancer or other cancers with an altered immune response. That is, the method according to the present invention is for preventing or treating cancer, in particular, the type of cancers identified herein or in a method for immune modulating the subject. Administration thereof may be by systemic application, by tumor application, into the vicinity of the tumor, intramuscular, oral, intranasal, intrapumonal, or combinations thereof.

For example, the OMVs are administered systemically or administered i.t. or into the vicinity of the tumor.

The immunogenic composition or the *Salmonella* strain according to present invention may be used in combination with conventional compounds and methods for treating cancer, used as a vaccine, for cytotoxic drug delivery or immunotherapeutic platform in general. In addition, suitable dosage forms and dosages can be determined by the skilled person by routine methods.

The present invention will be described further by a way of examples without limiting the same thereto.

EXPERIMENTAL PROCEDURES

Ethics Statement:

All animal experiments were performed according to guidelines of the German Law for Animal Protection and with permission of the local ethics committee and the local authority LAVES (Niedersächsisches Landesamt für Verbraucherschutz und Lebensmittelsicherheit) under permission number 33.9-42502-04-12/0713.

Strain Development:

Bacterial strains and plasmids are shown in Tab. S1.

TABLE S1

Bacterial strains and plasmids used herein

| Strain | Description |
|---|---|
| *Salmonella* Typhimurium strains | |
| SF102 | ΔlpxR9 ΔpagL7 ΔpagP8 ΔaroA |
| SF199 | ΔlpxR9 ΔpagL7 ΔpagP8 ΔaroA ΔydiV |
| SF200 | ΔlpxR9 ΔpagL7 ΔpagP8 ΔaroA ΔydiV ΔfliF:Frt-Kanamycin-Frt (FKF) |
| SF202 | ΔlpxR9 ΔpagL7 ΔpagP8 ΔaroA ΔydiV ΔfliF:FKF pHL304 |
| SF210 | ΔlpxR9 ΔpagL7 ΔpagP8 ΔaroA ΔfliHIJ |
| SF211 | ΔlpxR9 ΔpagL7 ΔpagP8 ΔaroA ΔfliHIJ ΔydiV |
| SF212 | ΔlpxR9 ΔpagL7 ΔpagP8 ΔaroA ΔydiV ΔfliF ΔeptA |
| SF213 | ΔlpxR9 ΔpagL7 ΔpagP8 ΔaroA ΔydiV ΔfliHIJ ΔeptA |
| *E. coli* strains | |
| EcN | *Escherichia coli* Nissle 1917 (Mutaflor) |
| Symbioflor-2 | *Escherichia coli* Symbioflor-2 (G1/2, G3/10, G4/9, G5, G6/7 and G8, pooled 1:1) |
| Plamids | |
| pHL304 | luxCDABE, Amp$^+$, Plac |

Bacteria were grown in LB medium at 37° C. P22 bacteriophage transduction was used for targeted gene deletion or one step inactivation as depicted in Datsento and Warner, PNAS, 200, 97(12), 6640-45. Deletion of ydiV was introduced to SF102 yielding SF199. Refer to Tab. S1 for genotypes. To obtain SF200, ΔfliF::Frt-Kanamycin-Frt (FKF) was transduced into SF199. For live imaging purposes, plasmid pHL304 encoding the luxCDABE operon conferring constitutive Lux-expression was transformed into bacteria via electroporation.

Preparation of Inoculum:

*Salmonella* and *E. coli* strains were grown overnight and sub-cultured to mid-log phase in LB media at 37° C. Symbioflor-2 was adjusted as described previously (Kocijancic et al., Oncotarget. 2016; 7:22605-22). In general, the bacteria were washed twice and adjusted to the desired $OD_{600}$ in pyrogen free PBS.

Murine Tumor Model:

Eight to twelve week old BALB/c mice (Janvier) were intradermalty inoculated with $5 \times 10^5$ syngeneic CT26 tumor cells (colorectal cancer, ATCC CRL-2638) or $5 \times 10^5$ F1.A11 tumor cells (fibrosarcoma) or $2 \times 10^6$ RenCa tumor cells in the right flank. Tumor development was monitored using caliper measurements. Upon reaching a tumor volume of approx. 150 mm$^3$ after 10 days, the mice were injected intravenously into the tail vein with $5 \times 10^6$ *Salmonella* or *E. coli*, unless otherwise specified.

Immunization:

Mice were immunized twice 5 and 4 weeks before tumor inoculation. For *Salmonella*, $5*10^6$ heat-inactivated S. *Typhimurium* UK-1 wild-type bacteria were used to immunize the mice using an intravenous route of inoculation. For *E. coli*, mice were orally administered by gavage with $5*10^8$ *E. coli* Symbioflor-2.

Therapeutic Benefit and Bacterial Burden:

Tumor development was monitored using caliper measurements for as long as tumors persisted or until confronted with a humane endpoint in terms of exceedingly large tumor size or morbidity. Body weight was monitored and used as general health indicator. A loss of body weight below 80% of the original body weight was incentive to euthanize a mouse. To determine the bacterial burden, blood, spleen, liver and tumors were harvested at 36 hours post infection. Tissue was homogenized and appropriated dilutions were plated on LB plates. CFUs were counted and the bacterial burden was calculated as total CFU per gram tissue.

TNF-α Measurement in Serum:

Blood samples were collected 1.5 and 3 h post infection. The TNF-α ELISA Max™ Standard Kit (Biolegend) was used to determine the TNF-α level in serum as a measure for the activation of the innate immune system. All steps were done according to the manufacturer's manual. Three different biological replicates were analyzed and a PBS treated group served as negative control.

Statistics:

Significance between two groups was determined using the nonparametric Mann-Whitney test, while one-way analysis of variance (ANOVA) with Bonferroni posttest was used to compare two or more groups. Significance levels of $p<0.05$, $p<0.01$, or $p<0.001$ were denoted with asterisks: *, , and *, respectively.

Results

Local Infection Retains a Tumor Therapeutic Effect

A therapeutic potential of our hexa-acylated Lipid A mutant 'SF100' harboring mutations ΔlpxR9, ΔpagL7 and ΔpagP8 and the influence of ΔaroA to this *Salmonella* vector has been described in the art. Here a corroborated first new strain—SF200—carrying additional mutations ΔydiV and ΔfliF is described. The products of these genes influence flagella synthesis and general physiology and were included to increase the potency of our vector strain.

Further, a beneficial effect is demonstrated for the second strain disclosed herein, namely SF210. As shown and discussed below, said strain has beneficial effects on treating cancer as well as with respect to immunomodulation of an individual.

To evaluate the performance of the two therapeutic strains in vivo, an inoculum of $5 \times 10^6$ bacteria was administered to syngeneic tumor bearing BALB/c mice by intravenous (i.v.) or intra-tumoral (i.t.) injection. The same infection dose was applied in most of previous studies, and thus allows direct comparison. Tumor development was assessed over a period of two weeks, or until the reach of humane endpoints. As seen in FIG. 1A, the *Salmonella* variant SF200 (ΔlpxR9 ΔpagL7 ΔpagP8 ΔaroA ΔydiV ΔfliF) induced complete clearance of CT26 tumors by 15 days of infection. The kinetic of tumor regression was comparable between both routes of inoculation (FIG. 1A). To corroborate results, we repeated our experiment with the more resistant renal carcinoma cell line RenCa. Here, SF200 also was able to clear the tumor, which was never observed with any other bacterial strain before. Finally, the most resistant fibro-sarcoma cell line F1.A11 was tested. Here, SF200 induced initial retardation. However tumors started to outgrow after day 3 post infection (FIG. 1B). Interestingly, this profile was observed regardless the route of infection, and may suggest that systemic infection is not essential for induction of a therapeutic effect.

To generalize this effect, we compared the therapeutic potency of probiotic *E. coli* upon i.t. and i.v. infection. The *E. coli* probiotics Symbioflor-2 (G1-G10) (Symbiopharm) and Mutaflor (*E. coli* Nissle, EcN, from e.g. Ardeypharm) have been explored for tumor therapy on several occasions and shown to exhibit inferior intrinsic potency in the CT26 model system compared to *Salmonella Typhimurium*. Again here, tumor development displayed a similar profile upon Symbioflor-2 infection between i.t. and i.v. inoculation (FIG.

1C). The efficacy of EcN, was even mildly improved upon i.t. infection, causing faster regression and complete clearance in the experimental group (FIG. 1D).

Figure 8:
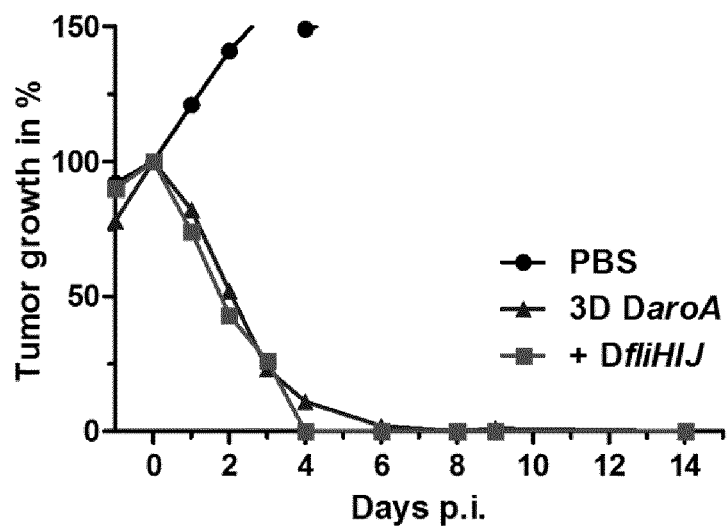
FIG. 8: shows the anti-tumor effect of the *Salmonella* strain SF210 ($\Delta$aroA, $\Delta$fliHIJ, $\Delta$lpxR9, $\Delta$pagL7, $\Delta$pagP8) in CT26 tumor bearing mice. CT26 tumors were treated with the strain according to the present invention and is compared to the control with PBS and the parent strain not containing $\Delta$fliHIJ. While normal tumor clearing always takes six to eight days as shown with the 3D$\Delta$aroA strain, the strain according to the present invention cleared all the tumors within four days. Of note, the 3D $\Delta$aroA strain killed about 20% of the mice during the experiment i.e. acquired additional pathogenicity due to the modification and will require additional attenuation.
Figure 9:
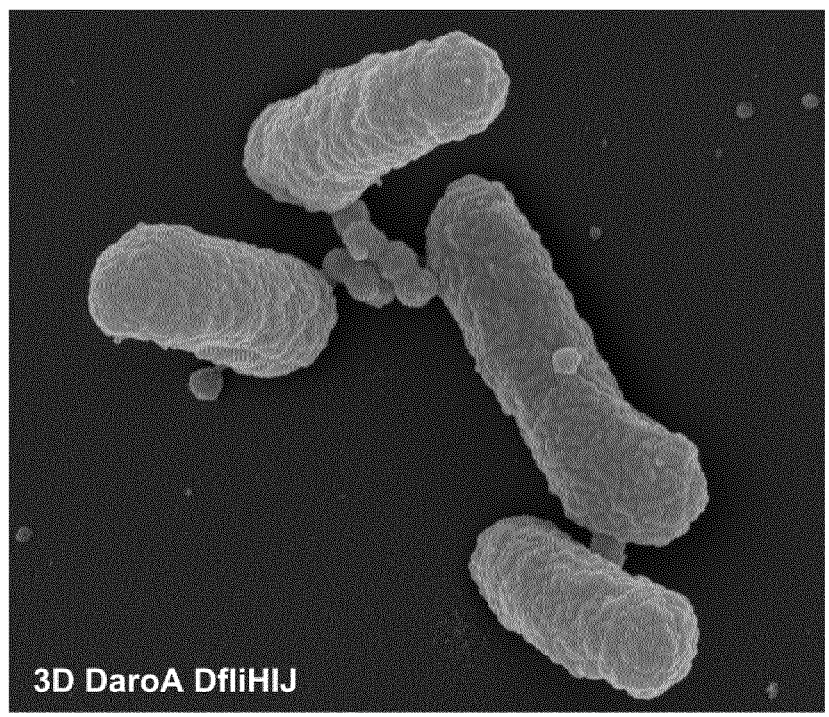
FIG. 9: OMV production by the strain SF210 according to the present invention. Shown is a scanning electron micrograph of the *Salmonella* mutant strain SF210 ($\Delta$pagP $\Delta$pagL $\Delta$lpxR $\Delta$aroA $\Delta$fliHIJ) indicating intensive production of OMV.

Similar results were obtained with the second strain identified above, namely strain SF210, see FIGS. 8 and 9.

In summary, direct bacterial inoculation into the target tumor retains intrinsic therapeutic potency as a customary intravenous route of infection.

Reduced Dissemination and Improved Health Status

Figure 2:
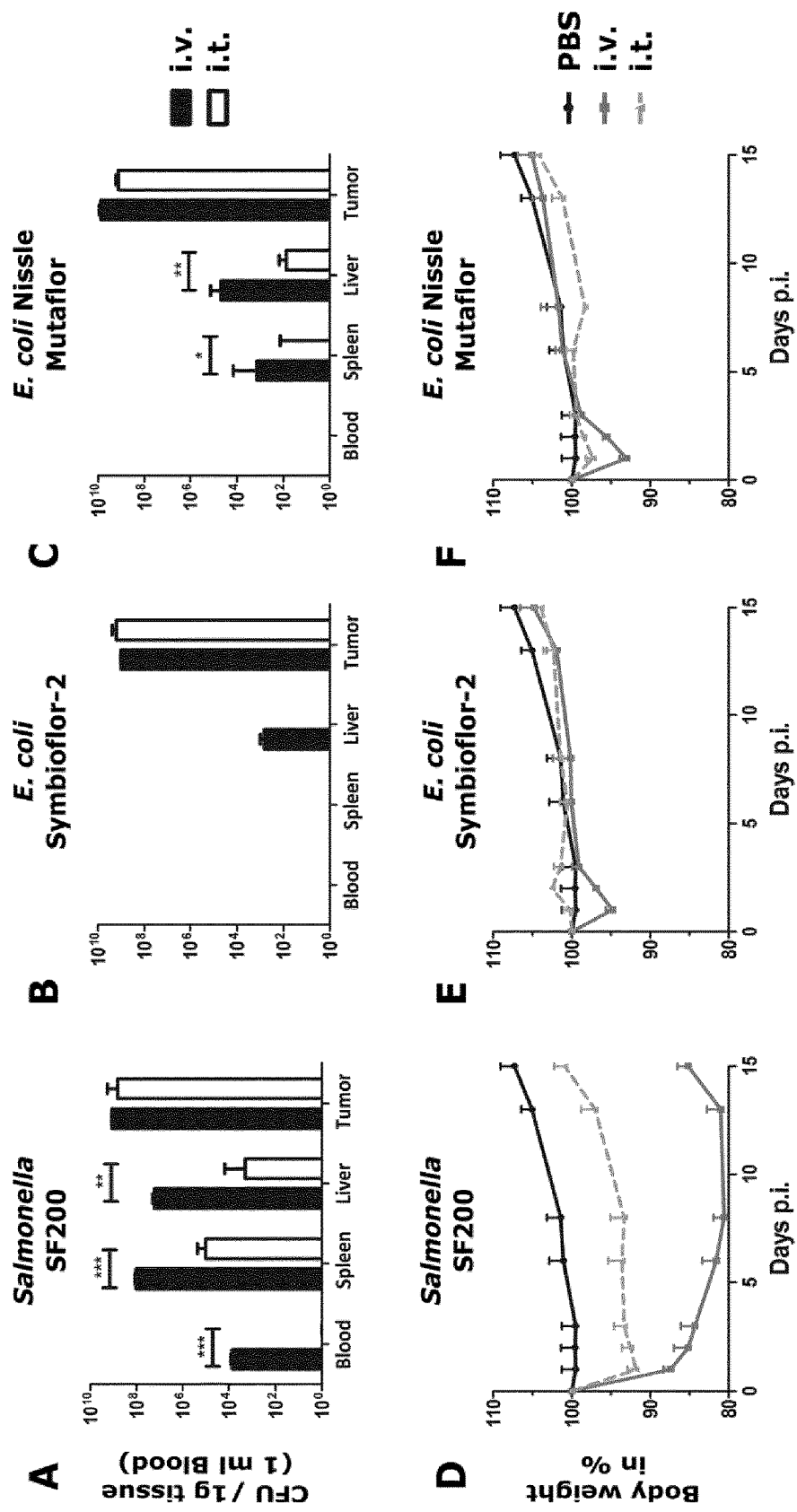
FIG. 2: Safety evaluation upon intravenous and intratumoral infection with *Salmonella* and probiotic *E. coli*. CT26 tumor bearing mice were infected i.v. and i.t. with $5 \times 10^6$ CFU SF200 ($\Delta$lpxR9 $\Delta$pagL7 $\Delta$pagP8 $\Delta$aroA $\Delta$ydiV MIT) and probiotic *E. coli*. (A-C) Blood, spleen, liver and tumor were analyzed for bacterial burden by plating serial dilutions of tissue homogenates. CFU counts were determined 48 hpi. Significantly lower numbers were observed during i.t. infections. (D-F) Body weight as indicator for the general health status of mice. Again, i.t. infection resulted in reduced body weight loss. PBS served as negative control. Displayed are medians with range. Results are representative of two independent experiments with five replicates per group. *, $p<0.05$; , $p<0.01$; *, $p<0.001$.

Tumor colonization remains a favorable feature of *Salmonella* because of direct oncolytic effects, either intrinsically preserved or reinforced through delivery of genetic cargo. Therefore, we tested *Salmonella* strain SF200 and SF210 for its intrinsic ability of tumor targeting upon systemic infection. We also compared it to colonization profiles upon i.t. infection. The i.t. route of bacterial inoculation should minimize dissemination and thus cause a safer phenotype for the host. As expected, SF200 did colonize the tumor with above $1 \times 10^8$ CFU/g tumor by 36 hpi (hours post infection) upon systemic infection (FIG. 2A). I.t. application resulted in similar high CFU in the tumor. As hypothesized, local inoculation did minimize dissemination. CFU in spleen and liver were reduced by a factor of $1 \times 10^3$ and $1 \times 10^4$, respectively, compared to i.v. infection. At this time point, lack of CFU in blood confirmed the absence of circulating salmonellae. The safer colonization profile was also reflected in the body weight loss, i.e. reflecting the general health status, of the hosts. I.t. infection caused a milder initial drop followed by quick recovery after 1 dpi (days post infection) (FIG. 2D). These results were corroborated with the probiotic strains of *E. coli*. Although a significant reduction in adverse colonization was evident with both Symbioflor-2 and EcN upon i.t. infection (FIG. 2B, C), the impact on host body weight was less prominent compared to *Salmonella* (FIG. 2E, F). The latter could be explained by a general superior health status upon systemic infection with probiotic bacterial strains.

Similar results were obtained with the second strain identified above, namely strain SF210.

Overall, an intra-tumoral route of inoculation does restrict dissemination of *Salmonella*, and thus improves the overall health status of murine subjects during BMTT.

Bacterial Application i.t. Induces an Effective Adaptive Anti-Tumor Immune Response Against CT26

I.v. infection with strains of *Salmonella* can induce a memory immune response against CT26. The effector mechanism mainly involves CD8+ T cells. Therapeutic potency by i.t. infection as seen in FIG. 1 implies that such an adjuvant effect may be preserved.

TNF-α represents an important readout for the tumor therapeutic effects and a systemic response. Hence, this cytokine was measured in serum upon infection with *Salmonella*. Even though locally administered, i.t. infection induced a strong systemic response of TNF-α at 1.5 hpi (FIG. 3A). Albeit significantly reduced compared to an i.v. route of infection, the serum levels obtained may be sufficient to induce local as well as systemic effects, and thereby explain the therapeutic results shown in FIG. 1.

To expand on the therapeutic response and to determine whether current dogma of anti-tumoral immune memory applies to i.t. infection, CT26-cleared mice were re-challenged with the same tumor cell line. These tumors did not establish, thus indicating that a memory response had been invoked (data not shown). In extension, we reconstituted Rag1$^{-/-}$ mice with CD8+ T cells isolated from wild-type BALB/c mice that had cleared CT26 via i.t. infection. Minimal tumor growth was observed by day 7 post transfer, upon which retardation and complete clearance occurred (FIG. 3B). Endpoint comparison of tumor volumes emphasizes a statistically significant effect across all replicates compared to controls reconstituted with naive T cells (FIG. 3C).

Altogether, local intra-tumoral infection is able to raise a systemic cytokine response and an effective anti-tumor CD8+ T cell response against CT26 tumors.

Secondary Tumor Targeting is not Restricted to a Systemic Intravenous Route of Infection The ability of *Salmonella* to intrinsically colonize CT26 tumors has been described previously, and may be exploited to deliver therapeutic cargo to secondary and surgically inaccessible tumors. This ability has been vastly explored via intravenous infections. It provides an important argument for such a route of application. We set out to explore whether SF200 applied i.t. could sufficiently escape the tumor site of inoculation to colonize "secondary" tumors located at different sites. Evidence collected thus far includes colonization of adverse organs, and a window of several hours, where bacteria are detected in the blood circulation upon i.t. infection. These are indications that may hypothetically also allow for colonization of other tumor niches.

Figure 4:
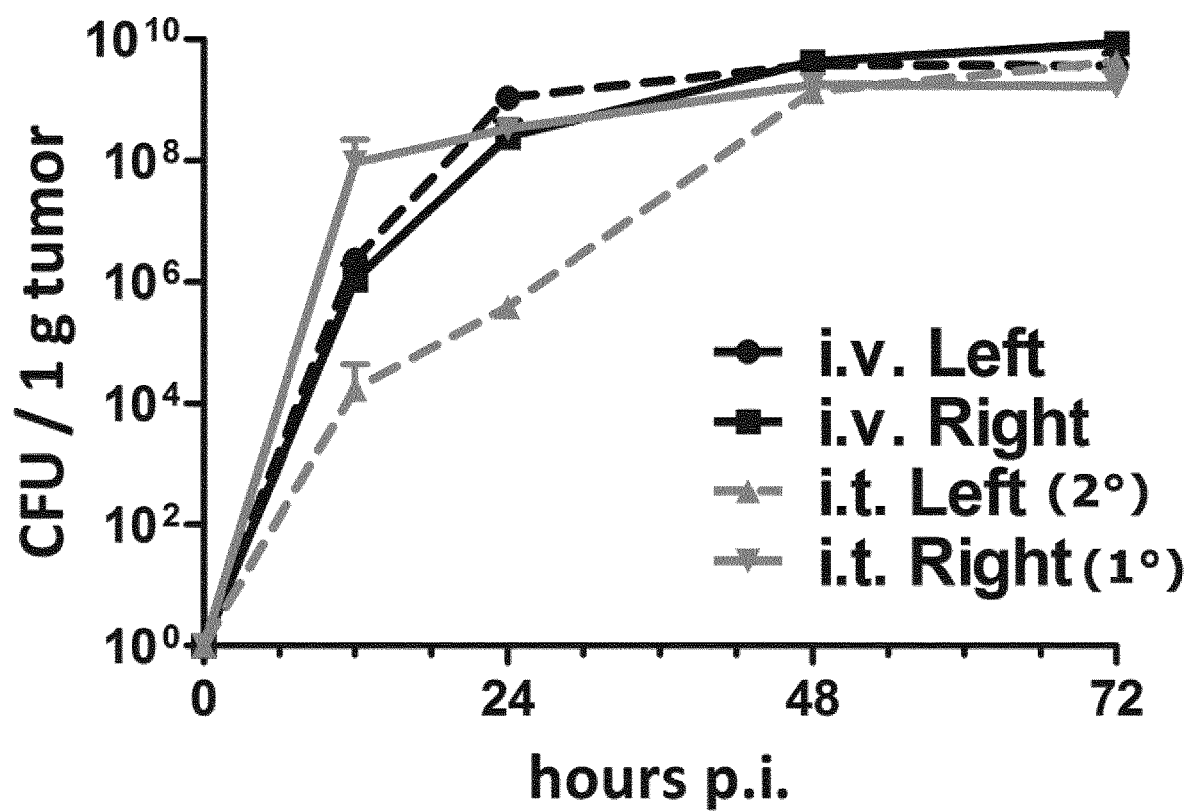
FIG. 4: Intra-tumoral infection allows effective colonization of secondary CT26 tumors. Bacterial colonization of tumors was determined by plating serial dilutions of tissue homogenates. CFU were analyzed 12, 24, 48 and 72 hpi to match imaging time points. For i.t. infection, primary and secondary tumors are denoted 1° and 2°, respectively. Displayed are medians with range. Results are representative of two independent experiments with five replicates in each group.

To trace the bacteria in vivo, we transformed a plasmid encoding the luxCDABE operon into our bacteria resulting in SF202 (SF200+pHL304). This construct ensures constitutive Luciferase (Lux) expression and is detectable via noninvasive in vivo imaging systems. This approach allowed us to track the progression of infection in an individual subject over time. As expected, Lux signals were detected 1 dpi with equal intensity in two anatomically separated CT26 tumors after i.v. infection. This observation was confirmed by plating (FIG. 4). During i.t. injection, the initial signal in the primary tumors was strong, as confirmed by plating. Interestingly, it was followed by a signal in the anatomically separated tumor at 2 dpi, which further intensified at 3 dpi. Plating data confirmed the qualitative observation and revealed bacterial counts of $1 \times 10^4$ CFU per gram in the secondary tumor within 12 hpi (FIG. 4). With the exception of delayed tumor invasion, a plateau of $1 \times 10^8$ CFU per gram in all tumors was substantiated under any circumstance. Similar results were obtained when tumors were placed at a more distant site (i.e. dorsal and abdominal) (data not shown).

Taken together, a superior safety standard, plasticity for dosing, retained adjuvanticity and a preserved ability of targeting secondary tumors, may render intra-tumoral application of bacteria an alternative route of application for progression through clinical trials and treatment of cancer patients with BMTT.

Immunized Tumor Bearing Mice are Less Sensitive to Bacterial Infection

Figure 5:
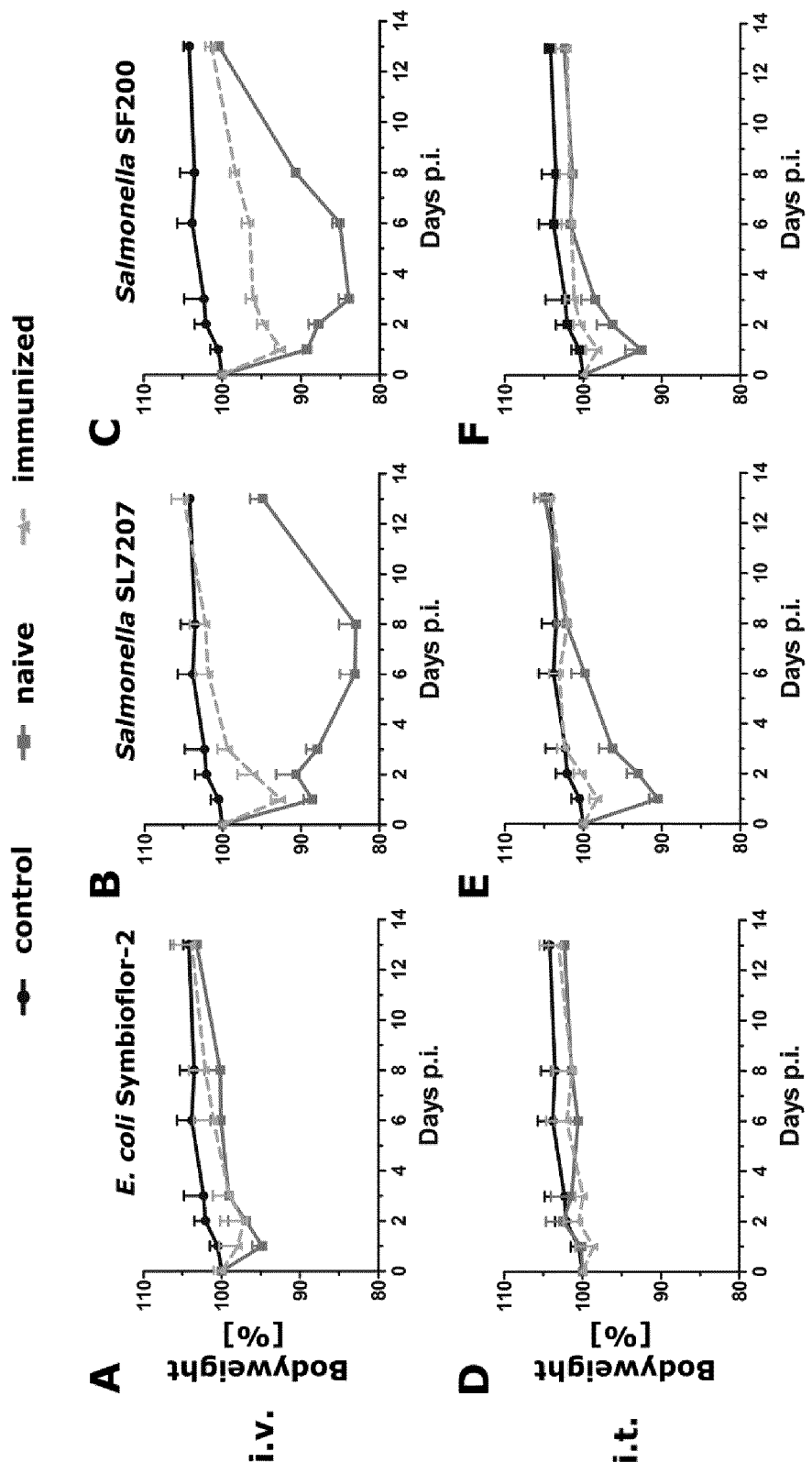
FIG. 5: Health burden of naïve and immunized mice upon infection with *Salmonella* and *E. coli*. Naïve and immunized CT26 tumor-bearing mice were infected intravenously (A-C) or intratumorally (D-F) with $5*10^7$ *E. coli* Symbioflor-2, $5*10^6$ SL7207 or $5*10^6$ SF200 ($\Delta$lpxR9 $\Delta$pagL7 $\Delta$pagP8 $\Delta$aroA $\Delta$ydiV $\Delta$fliF). Bodyweight was measured with a scale and used as indicator of general health. PBS served as a negative control. Displayed are values of mean±SD. Results are representative of two independent experiments with six replicates in each group.

The influence of a bacterial pre-exposure on BMTT susceptibility was investigated by treating naïve BALB/c mice with two doses of the corresponding bacteria spaced one week apart. To this end, heat-inactivated S. *Typhimurium* UK-1 was administrated intravenously or live *E. coli* Symbioflor-2 orally. To determine whether pre-exposure had conferred immunity against a re-challenge, immunized CT26 tumor bearing mice were infected intravenously (i.v.) or intratumorally with the corresponding bacteria (FIG. 5). In general, pre-exposure reduced the severity of infection as judged by the body weight loss and the general appearance of the mice (FIG. 5). As expected, this effect was more prominent for *Salmonella* compared to the probiotic *E. coli* strain as the latter affects the mice only to a minor extend in the first place. Interestingly, intratumoral (i.t.) rather than i.v. infection did influence immunized mice to a lesser extent compared to naïve mice. This emphasizes the higher safety profile of this route of inoculation (FIG. 5A-F). Beyond these macroscopic observations, the secondary infection induced a significantly decreased cytokine storm compared to the primary infection as revealed by measuring TNF-α levels in serum. Furthermore, pre-exposed mice displayed 80% less splenic colonization by salmonellae after infection and were less prone to splenomegaly. Altogether, these results demonstrate that pre-exposure improves the safety and decreases the immune pathology elicited by the bacteria at the same time. Therefore, it may also limit the efficacy of BMTT by these bacteria. The *Salmonella* strain according to the present invention, SF200 (ΔlpxR9 ΔpagL7 ΔpagP8 ΔaroA ΔydiV ΔfliF), developed for improved performance in BMTT, shows that neither the route of inoculation nor the immunization status significantly altered the tumor colonization in pre-exposed mice as determined by plating of CT26 tumor homogenates. Thus, even when applied systemically, SF200 can overcome the obstacle of bacterial immunity of the host and efficiently colonize tumor tissue.
Pre-Exposure Affects the Efficacy of Non-Optimized Strains Upon Infection As the microenvironment of the tumor is altered also after application of SF200, the pre-sensitized host response to bacterial infection could limit the potency of BMTT. To this end, naïve and immunized CT26 tumor bearing mice were intravenously infected with 5*10$^6$ *Salmonella* variants or 5*10$^7$ *E. coli* Symbioflor-2. As expected, most tumors of naïve mice regressed and were cleared by 14 dpi. However, *E. coli* Symbioflor-2 and the *Salmonella* variant SL7207 partially lost their ability to clear tumors in immunized in comparison to naïve mice. In case of infection with *E. coli*, 20% of the tumors regrew and in case of application of SL7207 only a single tumor out of five was cleared. Thus, immunization seriously limits the therapeutic benefit of these vector strains. In contrast, the *Salmonella* strain SF200 according to the present invention was able to clear all CT26 tumors also under immunized conditions. This suggests that the increased immunogenicity of SF200 may compensate for the immunity induced by pre-exposure.

Figure 6:
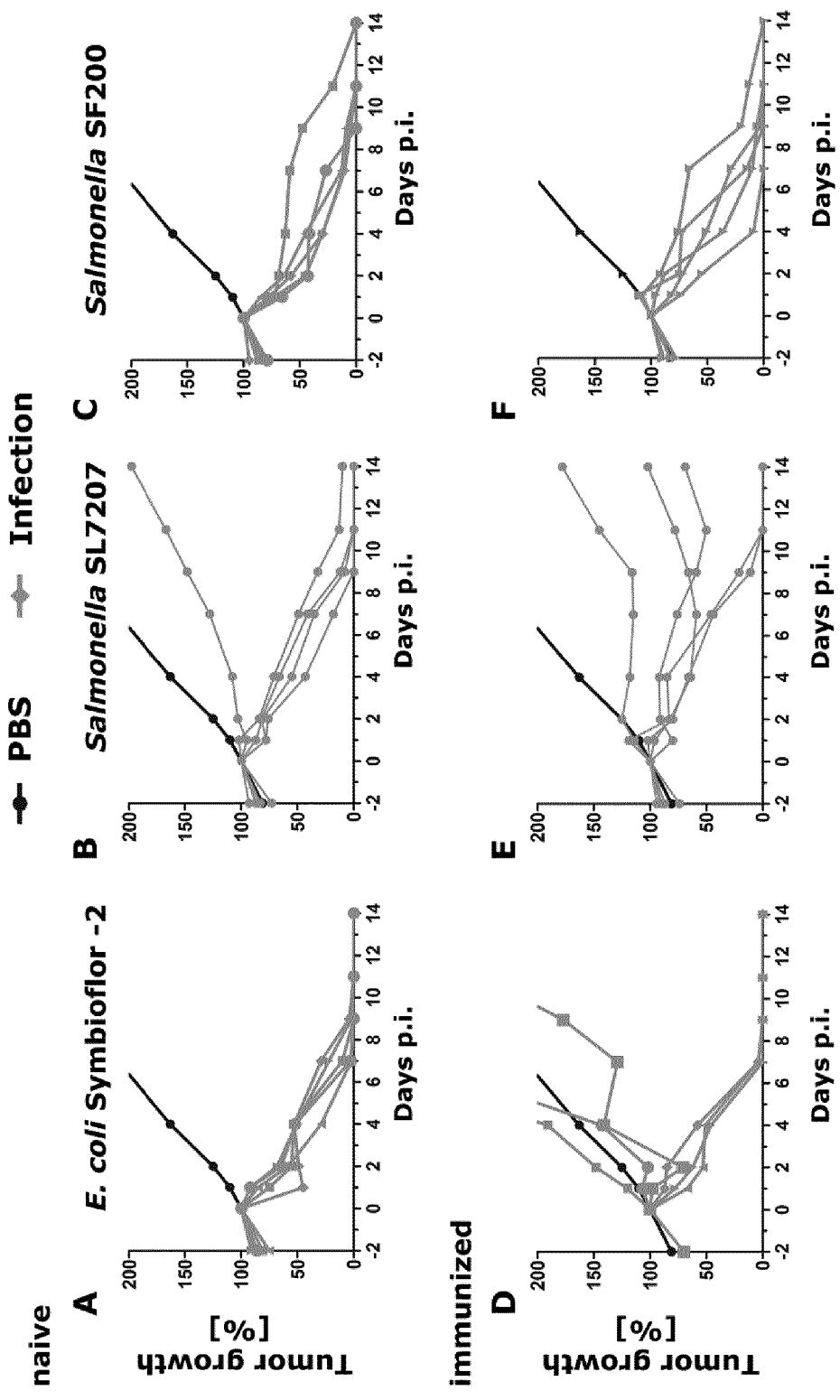
FIG. 6: Tumor development upon intratumoral infection with *Salmonella* and probiotic *E. coli* in naïve and immunized mice. Naïve (A-C) and immunized (D-F) CT26 tumor bearing mice were infected intravenously with $5*10^7$ *E. coli* Symbioflor-2, $5*10^6$ SL7207 or $5*10^6$ SF200 ($\Delta$lpxR9 $\Delta$pagL7 $\Delta$pagP8 $\Delta$aroA $\Delta$ydiV $\Delta$fliF). Tumor volumes were calculated on the basis of caliper measurements following infection with *E. coli* Symbioflor-2, SL7207 and SF200. PBS served as negative control. Tumor progression of individual mice is displayed. Results are representative of two independent experiments with five to seven replicates per group.

The negative influence of immunity was substantially more pronounced when the bacteria were administered intratumorally (FIG. 6). Both, *E. coli* Symbioflor-2 and *Salmonella* SL7207 lost more than 50% of their efficacy for tumor clearance in immunized compared to naïve mice (FIG. 6D-E). In contrast, the efficacy of the optimized *Salmonella* variant SF200 was not affected by pre-exposure of the mice to *Salmonella* and all CT26 tumors were cleared within 14 dpi (FIG. 6F). These results demonstrate that independent of the route of inoculation, highly potent vector strains are required to overcome the bacterial immunity in the host and to retain therapeutic efficacy. Otherwise the benefit observed under naïve conditions may be lost in a pre-sensitized population.

Essential Functional Components of SF200

Figure 7:
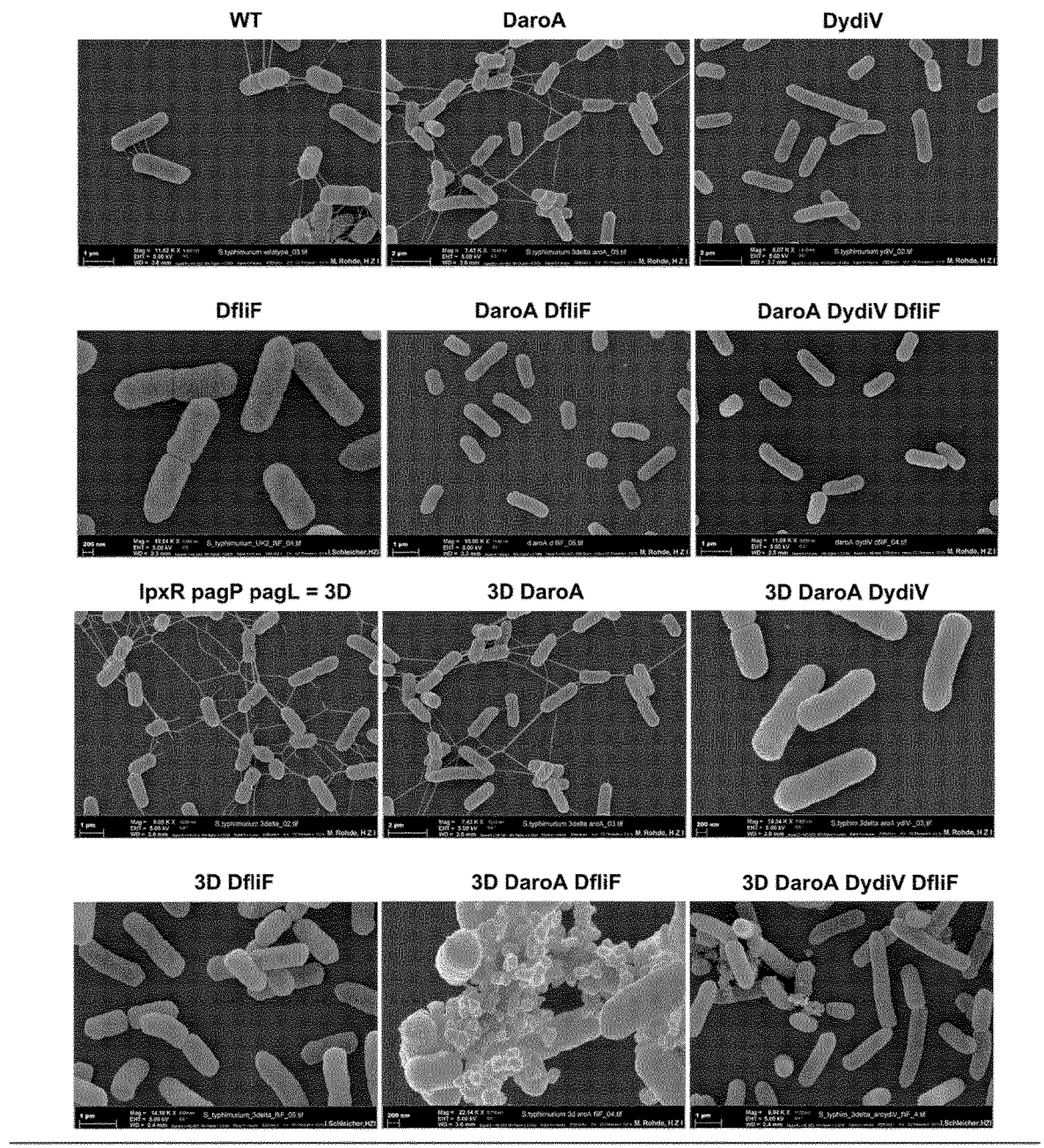
FIG. 7: Contribution of various gene deletions to OMV production and the therapeutic potential of *Salmonella* strains. Scanning electron microscopic pictures of *Salmonella* bearing single or combination deletions of the indicated genes. Schematically below, the therapeutic potential against colon carcinoma CT26 of such combinations is shown. As indicated, the ydiV deletion does not contribute to OMV formation but significantly improves the therapeutic potency.

As therapeutic agent, SF200 was shown to be dramatically superior to all strains tested by the inventors before. Since the composition of mutations in SF200 is highly complex, an analysis of the importance of single components within SF200 was carried out. All combinations of deleting mutations were introduced into the *Salmonella* and the bacteria were tested for OMV production and their therapeutic potency against the colon carcinoma. As shown in FIG. 7, the combination of deletion of fliF, aroA as well as lpxR9, pagP and pagL are all essential for the production of OMVs. However, for the superior performance of SF200 against the tumor in vivo the deletion of ydiV is helpful since the lack this gene product circumvents the downregulation of flagella components in vivo. In addition, it exhibits a strong influence of the general bacterial physiology. In addition, SF212 and SF213 are a strain on basis of SF200 and SF211, respectively that contains a deletion of eptA that increases the immunity and adjuvanticity of the lipidA.

As shown in FIG. 9, the second bacteria strain described in the examples demonstrates a production of the OMVs. These data demonstrate that mutations in the flagellin class II genes have superior effects. This is particularly true when combining them with mutations aroA gene as well as the lpxR gene, the pagP gene and the pagL gene as well as the eptA gene.

Figure 10:
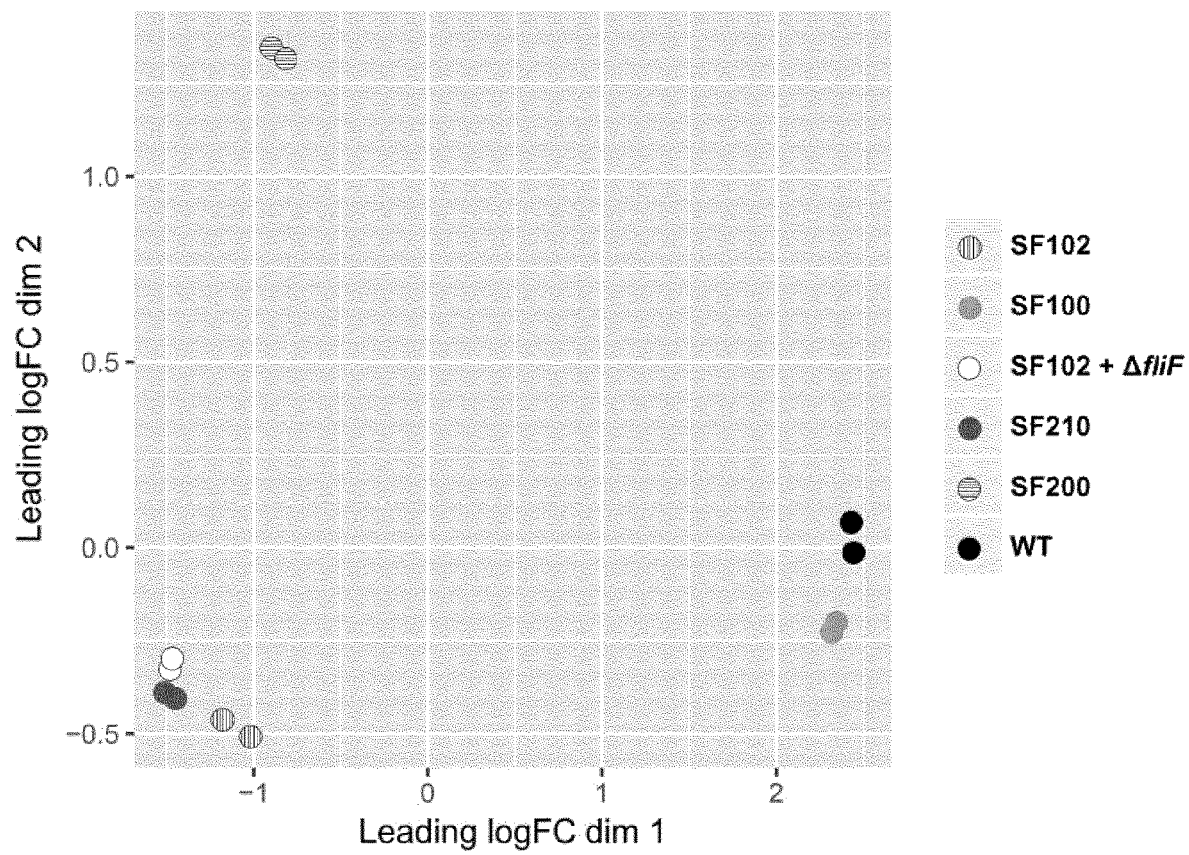
FIG. 10: Transcriptional analysis of *Salmonella* variants. MSD plot based on log$_2$ fold change of reads. Strains: SF100 ($\Delta$pagP $\Delta$pagL $\Delta$lpxR), SF102 ($\Delta$pagP $\Delta$pagL $\Delta$lpxR $\Delta$aroA), SF102+$\Delta$fliF, SF200 ($\Delta$pagP $\Delta$pagL $\Delta$lpxR $\Delta$aroA $\Delta$fliF $\Delta$ydiV) and SF210 ($\Delta$pagP $\Delta$pagL $\Delta$lpxR $\Delta$aroA $\Delta$fliHIJ). The similar position of SF102, SF102+fliF and SF201 indicate similar physiological conditions compared to WT and SF100 whereas SF200 the only strain that contains also a deletion of the gene ydiV shows a completely different genetic profil, indicating the strong influence of the mutation of the physiology of the bacteria.

Moreover, it is also beneficial to have mutations in the gene ydiV influencing the physiology of the bacteria (FIG. 10).

DISCUSSION

There are several ways to inactivate pathogenic bacteria for clinical application. Heat inactivation and formaldehyde fixation are examples of straightforward techniques, although they might result in reduced efficacy. Thus, bacterial attenuation has become the preferred strategy to accommodate safety. Considering Gram-negative bacterial candidates such as *Salmonella*, they are intrinsically prone to induce septic shock due to their LPS coat. Hence, modifications of LPS represent a rational choice to modify *Salmonella*. In accordance, we have placed extensive emphasis on such modifications to tailor strains of *Salmonella Typhimurium* with balanced properties of safety and intrinsic therapeutic benefit. Modifications shown to improve this balance include a hexa-acylated Lipid A structure implemented by the mutations ΔlpxR9, ΔpagL7 and ΔpagP8. This ensures high affinity binding of Lipid A to TLR4, and thus improved stimulation. Additionally, we could show that the metabolic mutation ΔaroA with its long-standing tradition provides therapeutic benefit to BMTT. This is most likely due to the down-regulation of arnT that is responsible for the modification of lipidA. In the respect also the deletion of eptA is active. Furthermore, structures like the flagellum, providing an immune stimulatory capacity via TLR5 may contribute relevant therapeutic power. In accordance, strain SF200 harbored the aforementioned mutations along with a deletion of ydiV and fliF. These genes encode a negative regulator of flagella synthesis (Takaya et al., 2012. Molecular Microbiology; 83(6):1268-84 and Wada et al., 2011. Journal of Bacteriology; 193(7):1600-1611) and a membrane bound protein required for flagella synthesis (Ueno et al., 1992. Journal of Molecular Biology; 227(3):672-7 and Kubori et al., 1997. Journal of Bacteriology; 179(3):813-817). In concert, the latter modifications would yield a *Salmonella* strain without functional flagella, however, rich in immune stimulatory flagella proteins expressed in vivo. Overall, the new strains according to the present invention performed well against our murine tumor models. It displayed efficacy against CT26, RenCa, and showed even transient therapeutic potency against the most rigid fibrosarcoma cell line F1.A11. The growth of RenCa as well as F1.A11 has been reported to be more rigid and unresponsive to *Salmonella* variants like SL7207 (Frahm M. et al., Bacterium-Mediated Tumor Therapy. 2015; 6:1-11).

The present results demonstrate that local intra-tumoral application provides an increased dosing variability compared to i.v. infection. In detail, equally potent tumor colonization over a greater dosing range of $5\times10^3$-$5\times10^6$ CFU was achieved with an i.t. application compared to an i.v. route of administration. In addition, side effects i.e. adverse colonization and body weight loss could be minimized via dose titration. We believe that the improved safety profile of i.t. versus i.v. inoculation will more readily allow dose escalation in clinical trials. Altogether, the local intra-tumor route of application exhibited greater plasticity, however, it needs to be validated with additional close-to-clinic strain candidates and tumor models.

Figure 3:
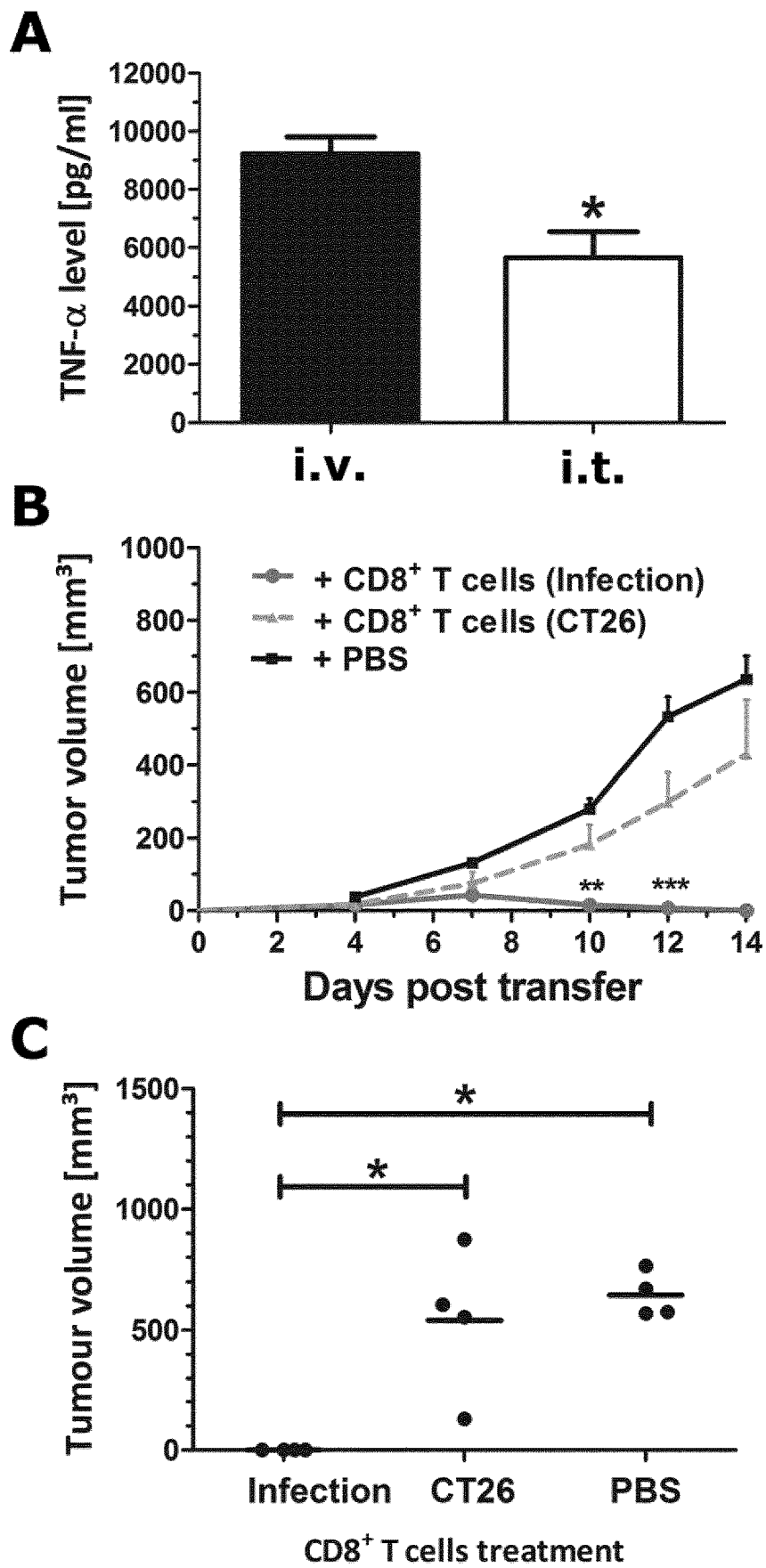
FIG. 3: Intra-tumoral infection induces innate and adaptive immune responses. (A) TNF-$\alpha$ levels in sera of CT26 tumor bearing mice isolated 1.5 h after infection with SF200 ($\Delta$lpxR9 $\Delta$pagL7 $\Delta$pagP8 $\Delta$aroA $\Delta$ydiV $\Delta$fliF). (B) CT26 tumor development in Rag1$^{-/-}$ mice reconstituted with CD8$^+$ T cells at the time of CT26 inoculation. $3 \times 10^6$ CD8$^+$ T cells were adoptively transferred from uninfected CT26 bearing mice ("CD8$^+$ T cells (CT26)") or CT26 tumor bearing mice treated with SF200 (("CD8$^+$ T cells (Infection) "). PBS served as negative control. (C) Endpoint tumor volume at day 14 post transfer. Displayed are values of mean±SEM. Results are representative of two independent experiments with five replicates per group. *, $p<0.05$; , $p<0.01$; *, $p<0.001$.

Histological manifestation of BMTT appeared consistent between i.t and i.v. infection. This suggests a similar therapeutic mechanism. The adjuvant effect was inherently preserved with i.t. infection, albeit the systemic cytokine response after i.t. application was slightly inferior to i.v. infection judged by levels of serum TNF-α (FIG. 3A). Nevertheless, this turned out to be sufficient to install effectiveness against CT26 tumors. Alternatively, i.t. infection may induce significantly higher local levels of such cytokines inside the tumor which could compensate for the systemic deficit. In principle, exaggerated responses induced by i.v. infection might not be required for successful CT26 therapy. Supposedly, even the lower adjuvanticity conferred by intra-tumoral infection or probiotic infection is sufficient to induce potent effects in this model. In support, and along the dogma, an effective CT26-specific cytotoxic T cell response could be induced by this alternate route of infection or alternate bacterial agents (FIG. 3).

In our study, *Salmonella* was shown to be able to colonize secondary tumors subsequent to local inoculation of the primary tumor. As such, it exhibited equal potency by 48 hpi compared to systemic application. Thus, *Salmonella* exploits its tumor targeting ability in spite of local application.

In conclusion, intra-tumoral infection preserves the full therapeutic potential of *Salmonella* while providing substantial safety benefit and may be deployed to support a recombinant bacterial solution in the fight against cancer.

Accidental or intentional exposure to phylogenetic relatives of the therapeutic bacteria such as *Salmonella* or *E. coli* causes immunity in patients. Therefore, a preexposed patient may become less responsive to the bacterial therapy. The present study aimed to evaluate the influence of such preexposure on BMTT. As such, preexposure generally greatly affected the mice and also the therapeutic effectiveness of BMTT. As expected, mice which had previously encountered the bacteria were less sensitive to secondary infections independent of whether the bacteria had been administered systemically or directly into the tumor. Pre-exposure also led to a significantly reduced cytokine response upon secondary exposure as determined by TNF-α levels in blood. Further, pre-exposure limited bacterial survival in vivo and reduced bacteria induced inflammation upon secondary infection. These observations highlight the importance of in-depth knowledge of the immunological background of patients before assigning a particular treatment. For instance, vaccination against salmonellae is often used to protect individuals that travel to endemic countries. Suspensions of probiotic *E. coli* are used to treat disorders of the gastrointestinal tract. Although immunity may be transient, protection often lasts for several years before the host again displays sensitivity. During this time, efficacy of BMTT with non-optimized bacteria may be limited due to a protective memory response.

TNF-α is a key mediator in BMTT. It induces necrosis in large parts of the tumor upon systemic infection. When we analyzed the tumor microenvironment under immunity conditions using immune histology, we found decreased TNF-α levels. Interestingly, immunity tremendously limited the extent of necrotic regions within the tumor. In addition, the typical appearance of infected tumors with salmonellae surrounding the necrotic area was also absent under these conditions. However, intratumoral application of bacteria was less prone to these alterations. A possible explanation for this observation could be that intratumorally administered bacteria are not exposed to the effector mechanisms of the immune system to a similar extent as during systemic administration. Although tumor colonization was indistinguishable between the two routes of injection after one week, one could argue that a hampered initial tumor colonization in immunized mice could explain the difference in histological observations. Upon systemic injection, fewer bacteria may initially reach the tumor because of a reduced cytokine response under immunity conditions. However, tumor invasion by merely a few bacteria is sufficient to ensure rapid bacterial proliferation to $10^9$ bacteria per gram tissue after 48 hpi, as demonstrated. We conclude that tumors represent an immune-privileged niche that can be filled to a specific level dependent on the bacterial species. This also implies that a strong immune induction by the bacteria is initially required to obtain a potent anti-tumor effect that leads to clearance of the tumor rather than an efficient early tumor colonization. This could explain why a presensitized mouse is less susceptible to bacterial cancer therapy using conventional strains.

However, the BMTT efficacy of the optimized *Salmonella* vector strain SF200 (ΔlpxR9 ΔpagL7 ΔpagP8 ΔaroA ΔydiV ΔfliF) according to the present invention was not affected under these circumstances. All tumors were successfully cleared, independent of the route of inoculation and immunization status. The homogenously hexa-acylated Lipid A structure resulting from mutations ΔlpxR9 ΔpagL7 ΔpagP8 renders the LPS molecule strong as ligand for the TLR4-MD2 complex and is extremely immune-stimulatory. The aroA deletion regulates many genes, and amongst such two genes (arnT and ansB) are usually involved in the immune escape of *Salmonella*. The deletion of eptA is further improving immunogenicity. The modifications affecting flagella synthesis and assembly resulted in improved immunogenicity and increased formation of OMVs. The ΔydiV deletion deregulates flagella synthesis under in vivo conditions and ensures that the stimulatory flagella proteins are not down regulated in the host. The ΔfliF mutation prevents productive assembly of the flagellar export apparatus.

The combination of these 6 genes i.e. these four properties resulted in a drastically increased therapeutic efficacy against cancer cells in vivo that could not simply be predicted. The same effect has been observed with the second construct, namely, the *Salmonella* vector strain SF210 having 8 mutations as outlined. Most likely, the production of OMVs by SF200 or SF210 or other strains according to the present invention is responsible in part for this improvement as OMVs represent a secretory system of the bacteria and stimulatory molecules might be transferred into immune or cancer cells. The OMVs might be generated because most of these mutations, besides improving immunogenicity in general, affect properties of the bacterial membrane. Bending of the membrane like in LPS mutants lead to OMV formation. In addition, the ydiV mutation circumvents the down regulation of the stimulatory flagella components under in vivo conditions.

The invention claimed is:

1. A mutated *Salmonella* strain comprising one or more mutations in each of a flagellin class II gene,
an aroA gene,
an IpxR gene,
a pagL gene,
a pagP gene, and
a ydiV gene,
wherein the one or more mutations in each of said genes alter the coding or non-coding sequence of said gene resulting in alteration of the expression of the protein encoded by said gene or alteration of the amino acid sequence.

2. The mutated *Salmonella* strain according to claim 1, wherein the flagellin class II gene includes at least one of fliF gene and fliHIJ gene.

3. The mutated *Salmonella* strain according to claim 1, wherein the IpxR gene is lpxR9 gene, wherein the pagL gene is pagL7 gene, and wherein the pagP gene is pagP8 gene.

4. The mutated *Salmonella* strain according to claim 3, further comprising one or more mutations in an eptA gene and optionally, one or more mutations in an arnT gene.

5. The mutated *Salmonella* strain according to claim 1, wherein the *Salmonella* strain is *Salmonella enterica.*

6. The mutated *Salmonella* strain according to claim 5, wherein the *Salmonella enterica* is serovar *Typhimurium* or serovar Typhi.

7. The mutated *Salmonella* strain according to claim 1, wherein said mutated *Salmonella* strain is attenuated.

8. The mutated *Salmonella* strain according to claim 1, wherein the strain has an increased formation of outer membrane vesicles (OMVs) as compared to a wild type strain.

9. An immunogenic composition comprising the mutated *Salmonella* strain according to claim 1 and a pharmaceutically acceptable carrier, effluent or diluent.

10. The immunogenic composition according to claim 9 further comprising an immunomodulatory molecule.

11. A method for treating cancer and/or inhibiting tumor growth in a subject in need thereof, comprising administering to the subject the mutated *Salmonella* strain according to claim 1.

12. The method according to claim 11, wherein said cancer is selected from the group consisting of colon cancer, rectum carcinoma, stomach cancer, fibrosarcoma, kidney cancer, skin cancer, brain cancer, spinal cord cancer, pancreatic cancer, liver cancer, mesenchymal cancer, prostate cancer, bladder cancer, breast cancer, lung cancer, bronchus cancer, trachea cancer, esophagus cancer, cervical cancer, brain cancer, uteri cancer, ovarian cancer, testicular cancer, thyroid cancer, lip cancer, oral cavity cancer, mesothelioma, large intestine cancer, bone cancer, lymphoma, and leukemia.

13. The method according to claim 11, wherein the mutated *Salmonella* strain is administered i) by systemic application, ii) by intra tumor application, iii) into the vicinity of the tumor, iv) intra-muscularly, v) orally, vi) intra-nasally, vii) intra-pulmonary or combinations thereof.

14. A method for transporting a compound to a target cell, comprising providing to the target cell the mutated *Salmonella* strain of claim 1, wherein the compound is selected from the group consisting of a toxic component, an immunomodulatory molecule, a small molecule, a large molecule, DNA, RNA, a protein, a peptide, and a prodrug converting enzyme.

* * * * *